(12) United States Patent
Liu

(10) Patent No.: US 10,722,402 B2
(45) Date of Patent: Jul. 28, 2020

(54) GOGGLE DEVICE AND BUCKLING MODULE THEREOF

(71) Applicant: ASWAN INTERNATIONAL CORP., Taipei (TW)

(72) Inventor: Wei-Ting Liu, Taipei (TW)

(73) Assignee: ASWAN INTERNATIONAL CORP., Taipei, Taiwan (CN)

( * ) Notice: Subject to any disclaimer, the term of this patent is extended or adjusted under 35 U.S.C. 154(b) by 30 days.

(21) Appl. No.: 16/191,064

(22) Filed: Nov. 14, 2018

(65) Prior Publication Data
US 2020/0146889 A1 May 14, 2020

(51) Int. Cl.
*A61F 9/02* (2006.01)

(52) U.S. Cl.
CPC .............. *A61F 9/027* (2013.01); *A61F 9/028* (2013.01)

(58) Field of Classification Search
CPC .... A61F 9/027; A61F 9/02; A61F 2007/0228; A63B 33/002; B63C 11/12; A44B 11/2553; Y10T 24/31; Y10T 24/314; Y10T 24/316; Y10T 24/26; Y10T 24/44077; Y10T 24/44085; Y10T 24/4412; Y10T 24/4415; Y10T 24/44025; Y10T 24/45539; Y10T 24/45225; Y10T 24/4555; Y10T 24/4556; Y10T 24/45602; Y10T 24/45775; Y10T 24/45874
USPC .......................................... 2/452; 24/265 BC
See application file for complete search history.

(56) References Cited

U.S. PATENT DOCUMENTS

| 2,715,223 | A | * | 8/1955 | Gay, Jr. | ..................... | A61F 9/02 |
| | | | | | | 2/439 |
| 5,617,589 | A | * | 4/1997 | Lacore | ................... | A41D 20/00 |
| | | | | | | 2/452 |
| 5,727,259 | A | * | 3/1998 | Kawamata | ......... | A44B 11/2592 |
| | | | | | | 2/452 |
| 5,802,622 | A | * | 9/1998 | Baharad | .................... | A61F 9/02 |
| | | | | | | 2/2.5 |
| 6,105,177 | A | * | 8/2000 | Paulson | .................. | A61F 9/027 |
| | | | | | | 2/431 |
| 6,276,795 | B1 | * | 8/2001 | Hall | ........................ | A61F 9/025 |
| | | | | | | 351/62 |

(Continued)

FOREIGN PATENT DOCUMENTS

WO    WO-2010068165 A1 *  6/2010  ............. A61F 9/027

*Primary Examiner* — Heather N Mangine
(74) *Attorney, Agent, or Firm* — Li & Cai Intellectual Property (USA) Office

(57) ABSTRACT

A buckling module of a goggle device includes a buckling structure, a flexible belt body and an inserting member fixed on the belt body. The buckling structure has an accommodating space and an entrance in spatial communication with the accommodating space. The buckling structure includes a front positioning portion and a rear positioning portion both arranged at two opposite sides of the entrance. When a front end portion of the inserting member is inserted into the accommodating space by passing through the entrance, the front end portion moves toward an inner surface of the front positioning portion, and a first portion of the belt body adjacent to the front end portion is resiliently squeezed by the front positioning portion, so that the squeezed portion of the belt body drives a rear end portion of the inserting member to move toward an inner surface of the rear positioning portion.

10 Claims, 15 Drawing Sheets

(56) References Cited

U.S. PATENT DOCUMENTS

| | | | | |
|---|---|---|---|---|
| 6,292,983 B1* | 9/2001 | Giaquinta | A44B 11/006 | 24/163 R |
| 6,349,419 B1* | 2/2002 | Chiang | A63B 33/002 | 2/428 |
| 6,367,091 B1* | 4/2002 | Chiang | A63B 33/002 | 2/428 |
| 6,389,653 B1* | 5/2002 | Matoba | A44B 11/006 | 24/265 AL |
| 6,611,965 B1* | 9/2003 | Lee | A61F 9/027 | 2/431 |
| 8,910,347 B1* | 12/2014 | Wilcox | B65D 63/109 | 24/16 R |
| 9,655,783 B2* | 5/2017 | McNeal | A61F 9/027 | |
| 2005/0155139 A1* | 7/2005 | Chiang | A63B 33/002 | 2/428 |
| 2009/0260136 A1* | 10/2009 | Chen | A61F 9/027 | 2/448 |
| 2009/0313746 A1* | 12/2009 | Wang | A61F 9/025 | 2/431 |
| 2012/0324638 A1* | 12/2012 | Tobia | A61F 9/02 | 2/439 |
| 2015/0049294 A1* | 2/2015 | Chin | G02C 1/06 | 351/86 |
| 2015/0128385 A1* | 5/2015 | Kuo | A44B 11/006 | 24/193 |
| 2015/0202087 A1* | 7/2015 | Chen | A61F 9/026 | 2/431 |
| 2016/0331591 A1* | 11/2016 | Kilduff | A61F 9/025 | |
| 2017/0035614 A1* | 2/2017 | Chen | A61F 9/027 | |
| 2017/0216098 A1* | 8/2017 | Li | A61F 9/025 | |
| 2018/0373064 A1* | 12/2018 | Chen | G02C 11/10 | |
| 2019/0142639 A1* | 5/2019 | Durham | A61F 9/02 | 2/439 |
| 2019/0192347 A1* | 6/2019 | Prugue | A61F 9/027 | |
| 2019/0343685 A1* | 11/2019 | Hung | G02C 1/06 | |

* cited by examiner

GOGGLE DEVICE AND BUCKLING MODULE THEREOF

FIELD OF THE DISCLOSURE

The present disclosure relates to a goggle, and more particularly to a goggle device and a buckling module thereof.

BACKGROUND OF THE DISCLOSURE

A conventional goggle includes a spectacle frame and a belt fastened to the spectacle frame. Two opposite ends of the belt are inseparably fixed at two opposite portions of the spectacle frame, respectively. Based on the above, since the belt cannot be changed from the spectacle frame in the structure of the conventional goggle, the appearance of the belt is determined after the conventional goggle is produced. Accordingly, if a user wants to have various appearances of the conventional goggle, the user would need to buy a plurality of goggles.

SUMMARY OF THE DISCLOSURE

In response to the above-referenced technical inadequacies, the present disclosure provides a goggle device and a buckling module thereof to effectively improve the issues associated with conventional goggles.

In one aspect, the present disclosure provides a goggle device, which includes a spectacle frame, a lens fastened to the spectacle frame, and a detachable belt. The spectacle frame includes two buckling structures respectively arranged on two opposite ends thereof. Each of the two buckling structures has an accommodating space and an entrance that is in spatial communication with the accommodating space. Each of the two buckling structures includes a front positioning portion and a rear positioning portion both of which are arranged at two opposite sides of the entrance, and includes a bottom wall facing the entrance. The detachable belt is detachably assembled with the two buckling structures, and the detachable belt includes an elongated and flexible belt body and two inserting members respectively fixed on two opposite ends of the belt body. Each of the two inserting members includes a front end portion and a rear end portion both of which are arranged on two opposite portions thereof, and the two inserting members are respectively inserted into the two buckling structures so as to be at a locked position. In each of the two buckling structures and the corresponding inserting member, when the front end portion is inserted into the accommodating space by passing through the entrance, the front end portion moves toward an inner surface of the front positioning portion, and a first portion of the belt body adjacent to the front end portion is resiliently squeezed by the front positioning portion, so that the squeezed first portion of the belt body drives the rear end portion to move toward an inner surface of the rear positioning portion. When each of the two inserting members is at the locked position, a movement of each of the two inserting members in the accommodating space of the corresponding buckling structure is restricted by the front positioning portion and the rear positioning portion.

In one aspect, the present disclosure provides a buckling module of a goggle device, which includes a buckling structure, a flexible belt body, and an inserting member. The buckling structure is arranged on an end of a spectacle frame. The buckling structure has an accommodating space and an entrance that is in spatial communication with the accommodating space. The buckling structure includes a front positioning portion and a rear positioning portion both of which are arranged at two opposite sides of the entrance, and includes a bottom wall facing the entrance. The inserting member is fixed on an end of the belt body. The inserting member includes a front end portion and a rear end portion both of which are arranged on two opposite portions thereof, and the inserting member is inserted into the buckling structure so as to be at a locked position. When the front end portion of the inserting member is inserted into the accommodating space by passing through the entrance, the front end portion moves toward an inner surface of the front positioning portion, and a first portion of the belt body adjacent to the front end portion is resiliently squeezed by the front positioning portion, so that the squeezed first portion of the belt body drives the rear end portion to move toward an inner surface of the rear positioning portion. When the inserting member is at the locked position, a movement of the inserting member in the accommodating space of the buckling structure is restricted by the front positioning portion and the rear positioning portion.

Therefore, the spectacle frame of the goggle device in the present disclosure is formed with the buckling structure that is cooperated with an inserting member and a belt body, so that the buckling structure is capable of being stably assembled with the detachable belt. Accordingly, the detachable belt on the spectacle frame of the goggle device in the present disclosure can be changed according to different requirements, so that the goggle device 100 can have various appearances.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
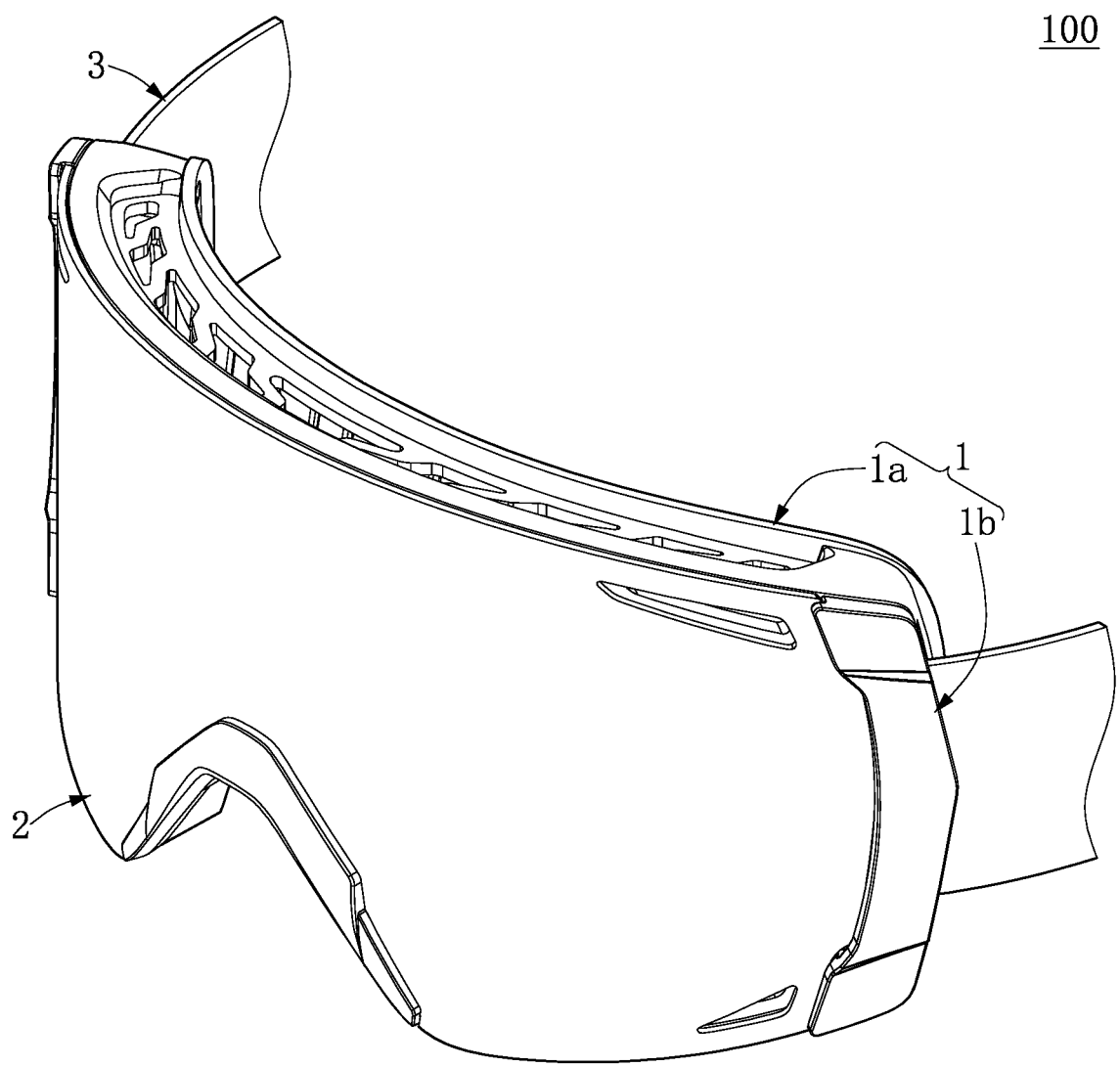
FIG. 1 is a perspective view of a goggle device according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
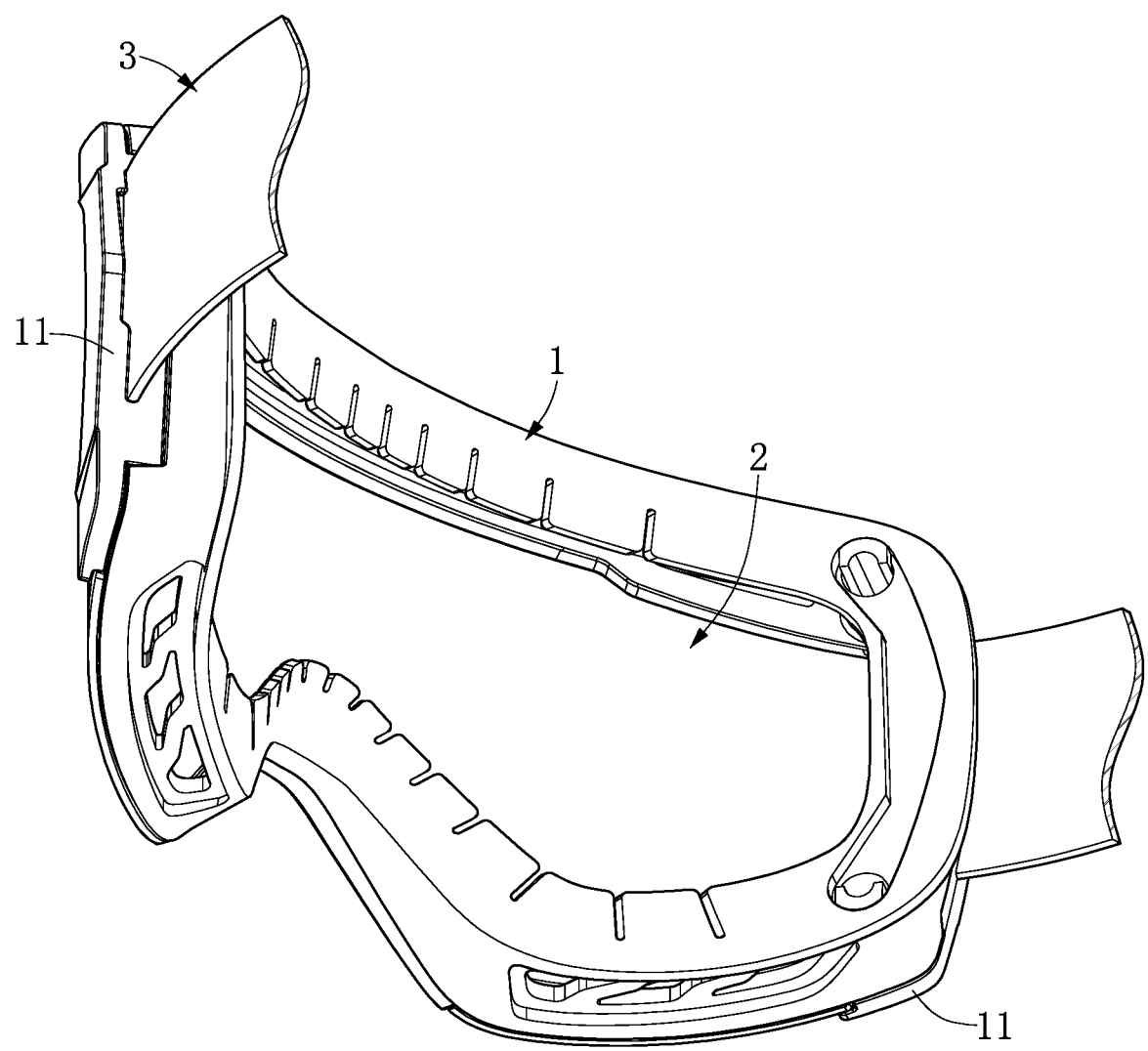
FIG. 2 is a perspective view of the goggle device from another angle of view.
Figure 3:
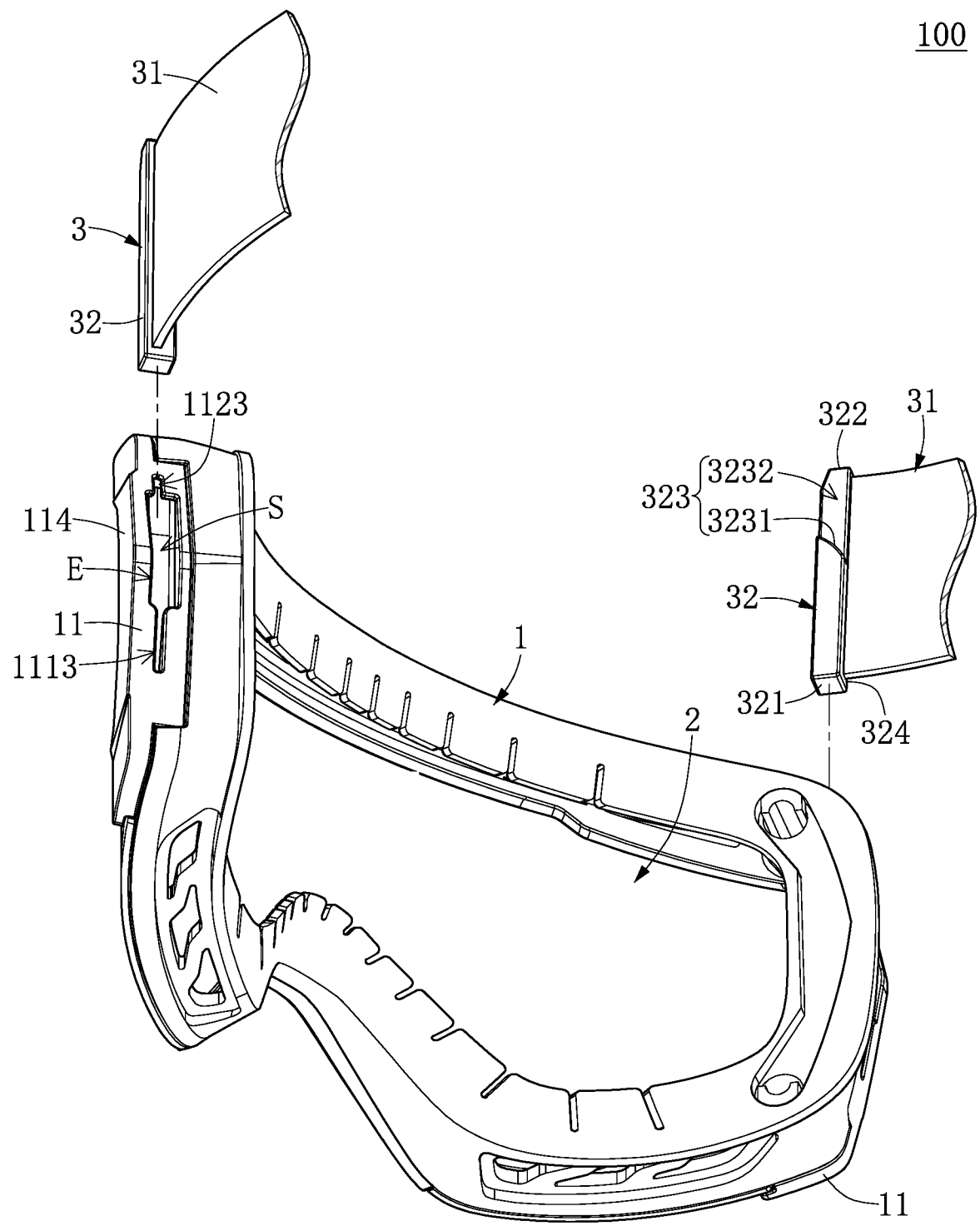
FIG. 3 is an exploded view of FIG. 2.

Referring to FIG. 1 to FIG. 15, an embodiment of the present disclosure provides a goggle device 100 for being worn on (e.g., being gaplessly attached to) a user's face so as to protect the user's eyes. The goggle device 100 in the present embodiment is a snow goggle device that can be applied to a snow environment, but the present disclosure is not limited thereto. As shown in FIG. 1 to FIG. 3, the goggle device 100 in the present embodiment includes a spectacle frame 1, a lens 2 fastened to the spectacle frame 1, and a detachable belt 3 detachably assembled with the spectacle frame 1. The following description discloses the structure and connection relationship of each component of the goggle device 100.

As shown in FIG. 3, the spectacle frame 1 includes two buckling structures 11 respectively arranged on two opposite ends thereof, and the detachable belt 3 is detachably assembled with the two buckling structures 11. Each of the two buckling structures 11 has an accommodating space S and an entrance E that is in spatial communication with the accommodating space S. Moreover, the detachable belt 3 includes a flexible belt body 31 having an elongated shape and two inserting members 32 respectively fixed on two opposite ends of the belt body 31. Each of the two inserting members 32 has a longitudinal direction that is substantially perpendicular to a longitudinal direction of the belt body 31.

Specifically, the two inserting members 32 of the detachable belt 3 are respectively inserted into the two buckling structures 11 of the spectacle frame 1 so as to be located at a locked position (as shown in FIG. 2). In addition, each of the two inserting members 32 of the goggle device 100 is configured to be pressed by a flat structure (e.g., a coin) so as to move from the locked position to an unlocked position (as shown in FIG. 3), and the detachable belt 3 of the goggle device 100 can be disassembled from the spectacle frame 1 by flat structures with different sizes.

It should be noted that, the goggle device 100 in the present embodiment is provided with the spectacle frame 1 cooperating with the lens 2 and the detachable belt 3, but the present disclosure is not limited thereto. For example, one of the two buckling structures 11, the corresponding belt body 31, and the corresponding inserting member 32 can be jointly defined as a buckling module, and the buckling module in other embodiments of the present disclosure can be applied to other devices.

Moreover, as the two buckling structures 11 are of the same or symmetrical structure, the following description discloses the structure of one of the two buckling structures 11 and a corresponding portion of the detachable belt 3 (i.e., a part of the belt body 31 and the corresponding inserting member 32) for the sake of brevity, but the present disclosure is not limited thereto. For example, in other embodiments of the present disclosure, the spectacle frame 1 of the goggle device 100 can be formed with only one buckling structure 11 arranged on an end portion thereof, and the other end portion of the spectacle frame 1 can have a structure different from the buckling structure 11.

Figure 4:
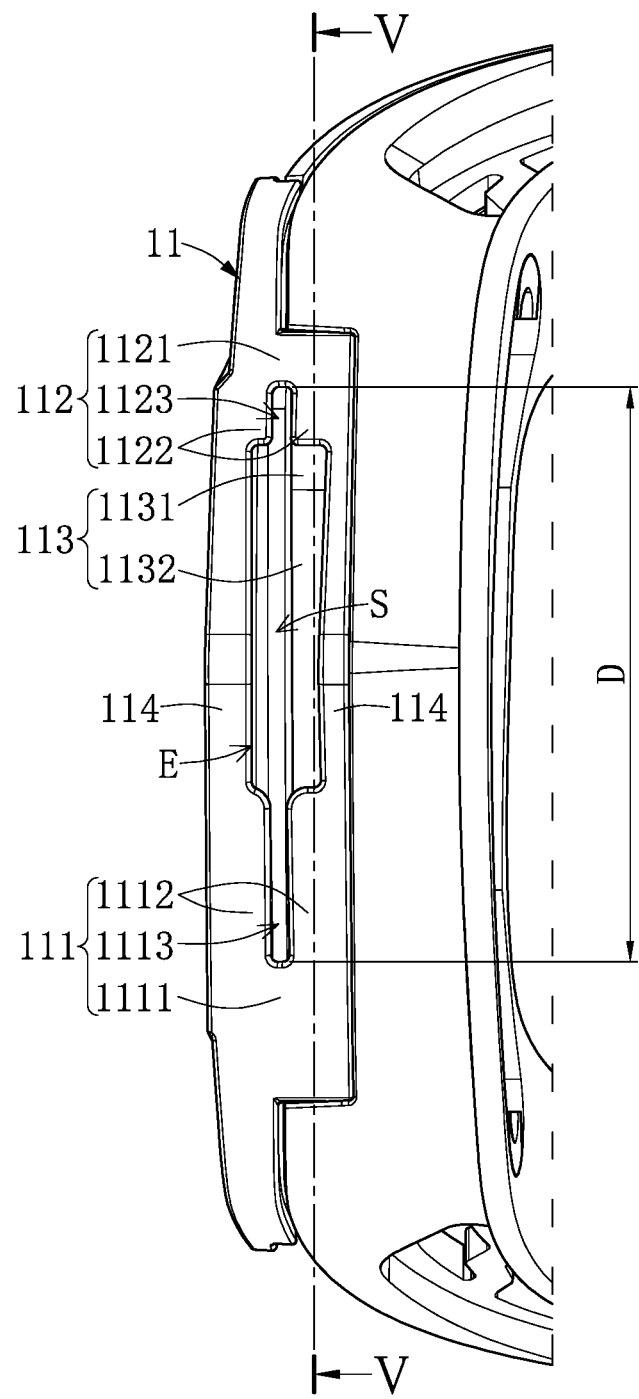
FIG. 4 is a side view of the goggle device showing a buckling structure.
Figure 5:
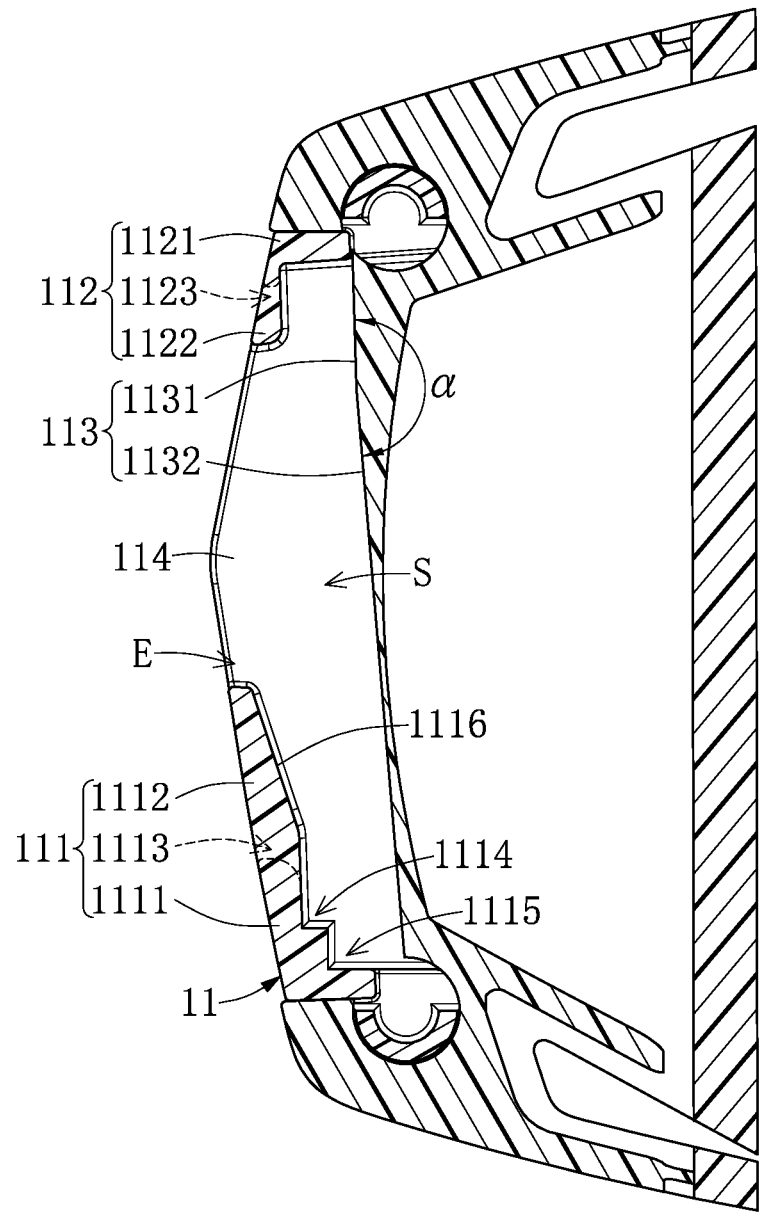
FIG. 5 is a cross-sectional view taken along line V-V of FIG. 4.
Figure 6:
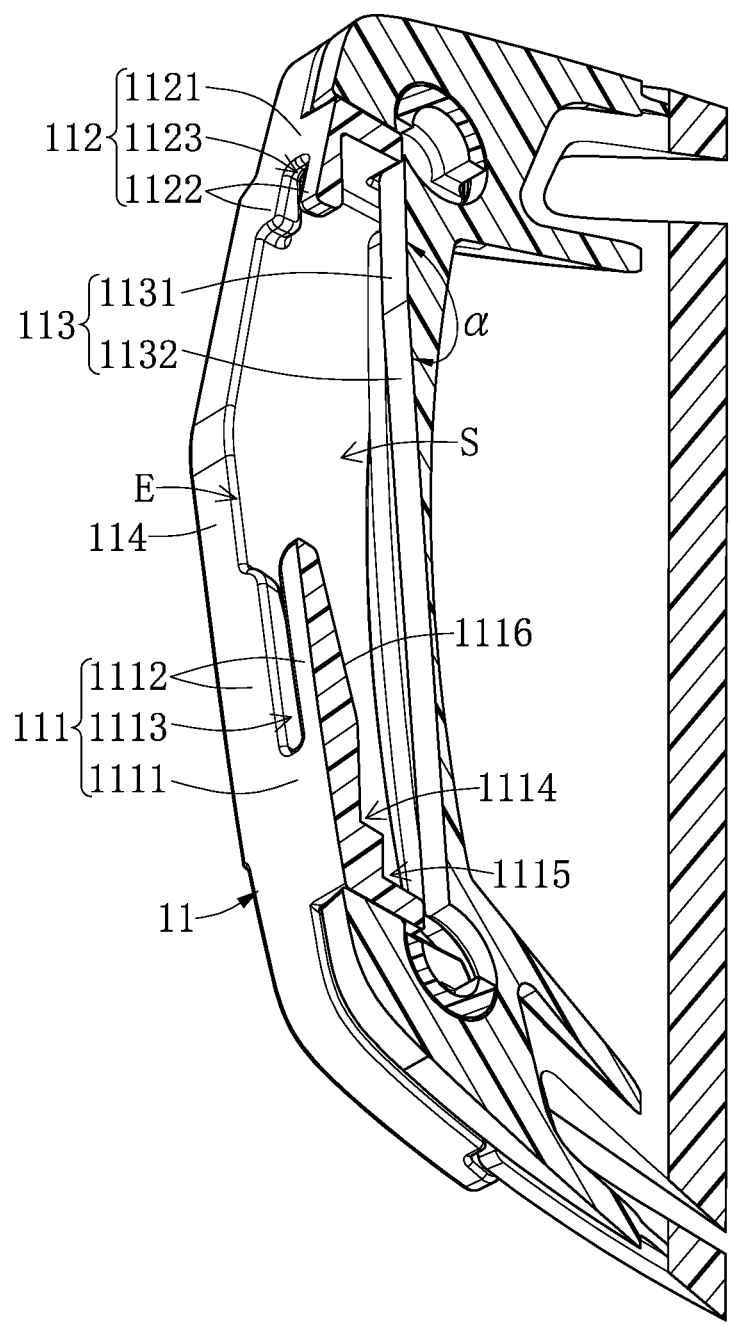
FIG. 6 is a perspective view of FIG. 5.

As shown in FIG. 4 to FIG. 6, the buckling structure 11 includes a front positioning portion 111 and a rear positioning portion 112 both of which are arranged at two opposite sides of the entrance E, and includes a bottom wall 113 facing the entrance E and two long side walls 114 connected to the bottom wall 113. The front positioning portion 111, the rear positioning portion 112, the bottom wall 113, and the two long side walls 114 jointly and surroundingly define the accommodating space S. An inner surface of the front positioning portion 111, an inner surface of the rear positioning portion 112, and inner surfaces of the two long side walls 114 jointly define the entrance E that is in spatial communication with the accommodating space S.

The front positioning portion 111 includes a front base 1111 and two front retaining ribs 1112 that extend from the front base 1111 toward the entrance E. The two front retaining ribs 1112 are arranged apart from each other, and are respectively connected to the two long side walls 114. The front base 1111 and the two front retaining ribs 1112 surroundingly define a front slit 1113 that is in spatial communication with the accommodating space S and the entrance E.

Moreover, the inner surface of the front positioning portion 111 (e.g., a part of an inner surface of the front base 1111 facing the bottom wall 113 and a part of an inner surface of each of the two front retaining ribs 1112 that face the bottom wall 113 and is adjacent to the front base 1111) includes a first step 1114 and a second step 1115. The first step 1114 is closer to the entrance E and the bottom wall 113 than the second step 1115. Each of the two front retaining ribs 1112 includes a guiding surface 1116 arranged on the inner surface thereof facing the bottom wall 113 and connected to the first step 1114. In other words, the guiding surface 1116 slantingly extends from an edge of the first step 1114 toward the entrance E, and the edge of the first step 1114 is arranged away from the second step 1115. A virtual extension of the guiding surface 1116 passes through the second step 1115, and does not pass through the first step 1114. Accordingly, an object (e.g., the inserting member 32) contacting the guiding surface 1116 can be guided to move toward the second step 1115 by the guiding surface 1116.

As shown in FIG. 4 to FIG. 6, the rear positioning portion 112 includes a rear base 1121 and two rear retaining ribs 1122 that extend from the rear base 1121 toward the entrance E. The two rear retaining ribs 1122 are arranged apart from each other, and are respectively connected to the two long side walls 114. The two rear retaining ribs 1122 respectively face the two front retaining ribs 1112. The rear base 1121 and the two rear retaining ribs 1122 surroundingly define a rear slit 1123 that is in spatial communication with the accommodating space S and the entrance E. It should be noted that, one of the two rear retaining ribs 1122 having a larger width in the present embodiment is defined as an unlocking rib 1122.

Moreover, an inner surface of the rear base 1121 is formed with a slot-like structure, and an inner surface of each of the two rear retaining ribs 1122 facing the bottom wall 113 is substantially coplanar with a surface of the first step 1114 that is arranged away from the bottom wall 113. A bottom of the front slit 1113 is substantially arranged on a center part of the surface of the first step 1114. A maximum distance D between the front slit 1113 and the rear slit 1123 (i.e., a distance D between the bottoms of the front slit 1113 and the rear slit 1123) is substantially equal to a width W of a portion of the belt body 31 adjacent to the inserting member 32 (as shown in FIG. 7).

The bottom wall 113 includes a plane segment 1131 arranged adjacent to the rear positioning portion 112 and a slanting segment 1132 extending from the plane segment 1131. A projected region defined by orthogonally projecting the unlocking rib 1122 onto the bottom wall 113 is entirely located on the plane segment 1131, and covers at least 60% of the plane segment 1131, but the present disclosure is not limited thereto. Moreover, the plane segment 1131 and the slanting segment 1132 in the present embodiment have an angle α there-between that is within a range of 150-185 degrees and is preferably within a range of 181-185 degrees, but the present disclosure is not limited thereto. In addition, the angle α between the plane segment 1131 and the slanting segment 1132 is preferably greater than an angle between the guiding surface 1116 of the front positioning portion 111 and the surface of the first step 1114 that is arranged away from the bottom wall 113.

Figure 7:
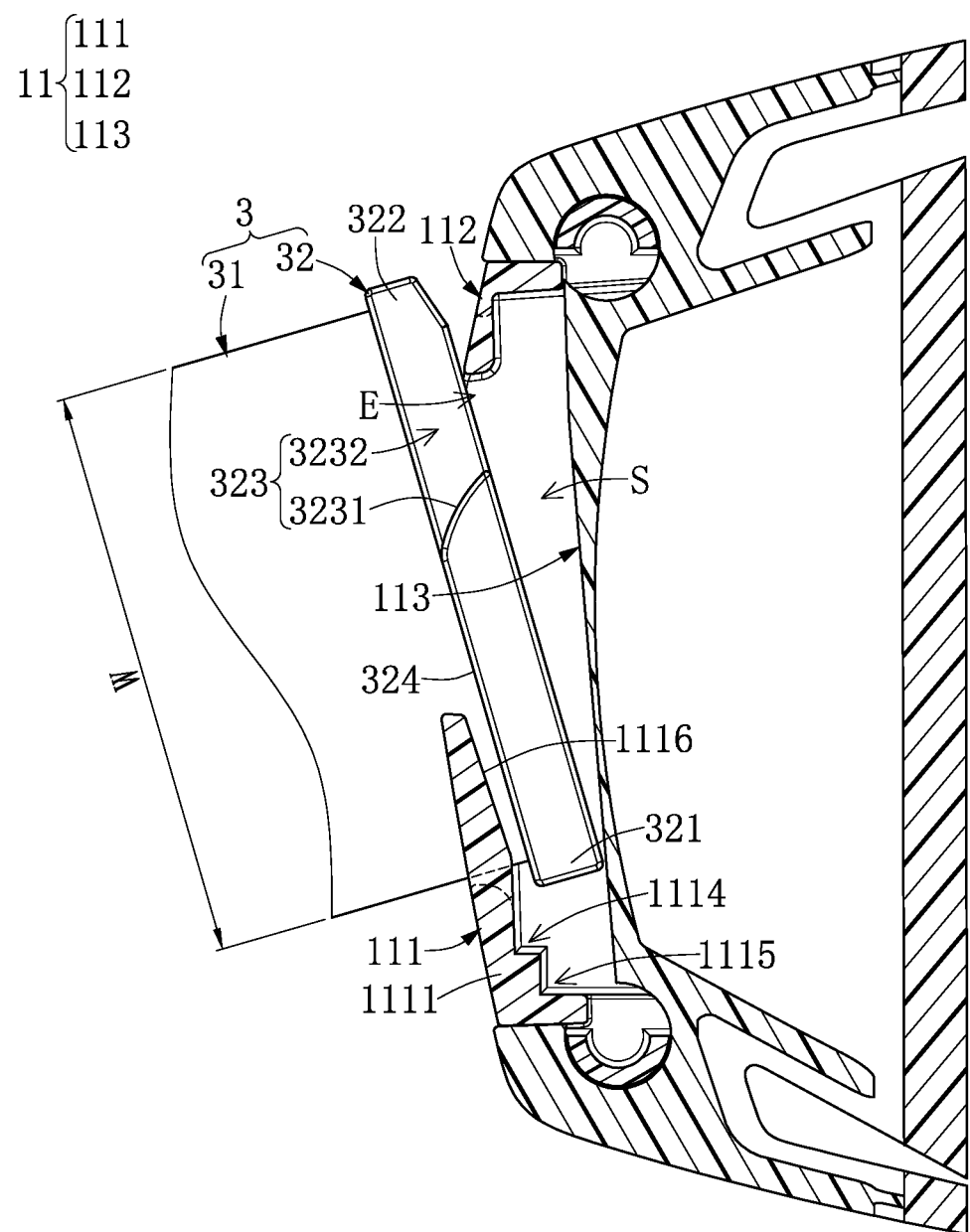
FIG. 7 is a cross-sectional view showing the buckling structure that is used to receive a part of an inserting member.
Figure 8:
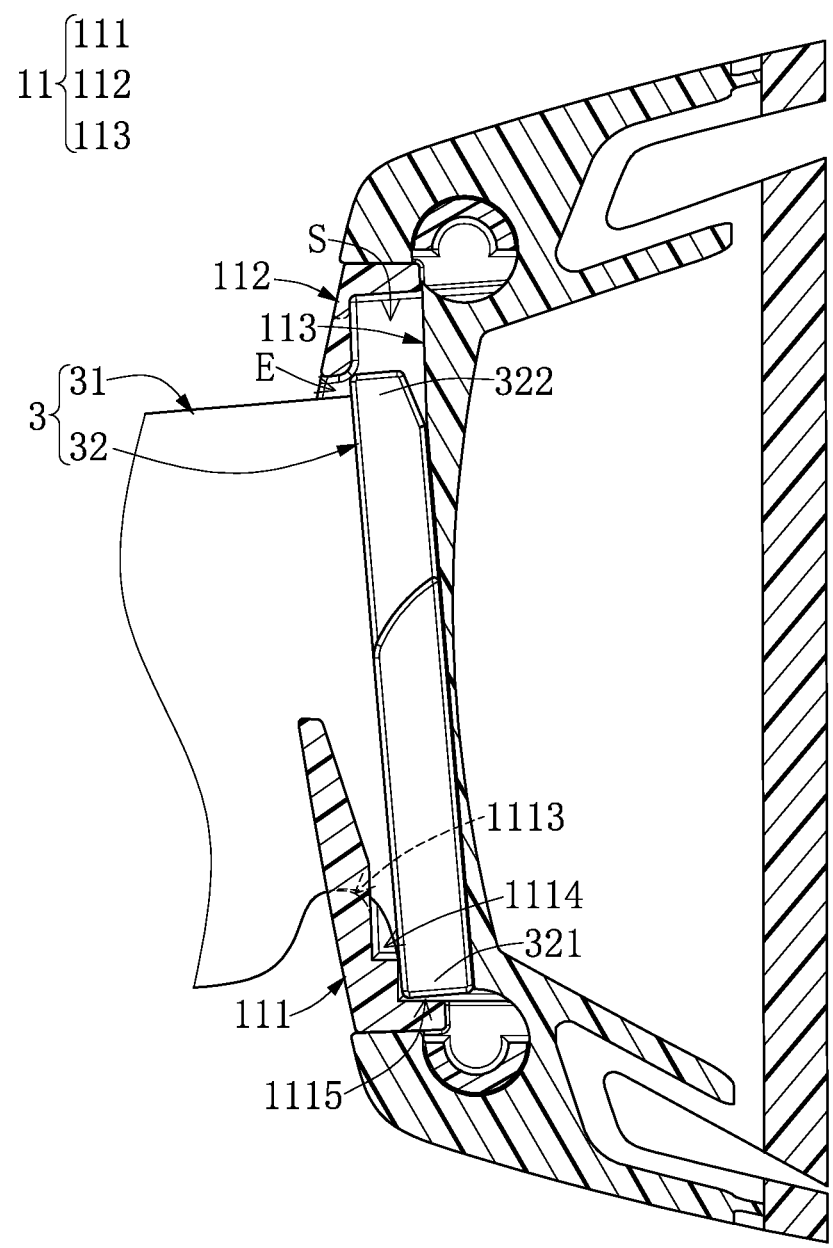
FIG. 8 is a cross-sectional view showing the buckling structure that receives the inserting member.

As shown in FIG. 3 and FIG. 7, the inserting member 32 is an elongated structure, and includes a front end portion 321 and a rear end portion 322 both of which are arranged on two opposite portions thereof. The inserting member 32 includes a concave portion 323 recessed in the rear end portion 322. In the present embodiment, an end of the belt body 31 is inserted into and fixed in the inserting member 32 by passing through a top surface 324 of the inserting member 32, and the concave portion 323 of the inserting member 32 includes an arced surface 3231 with an edge connected to a middle part of the top surface 324.

In other words, the inserting member 32 has a notch 3232 recessed in a corner of the top surface 324, and the notch 3232 is formed between the arced surface 3231 and a distal end of the rear end portion 322. Moreover, a distance between the arced surface 3231 and a distal end of the front end portion 321 gradually increases along a direction away from the top surface 324 (e.g., a rightward direction as shown in FIG. 7).

Each component of the goggle device 100 of the present embodiment is disclosed in the above description, and the following description describes the relationship between each of the two buckling structures 11 and a corresponding portion of the detachable belt 3 (i.e., a corresponding portion of the belt body 31 and the corresponding inserting member 32).

Figure 9:
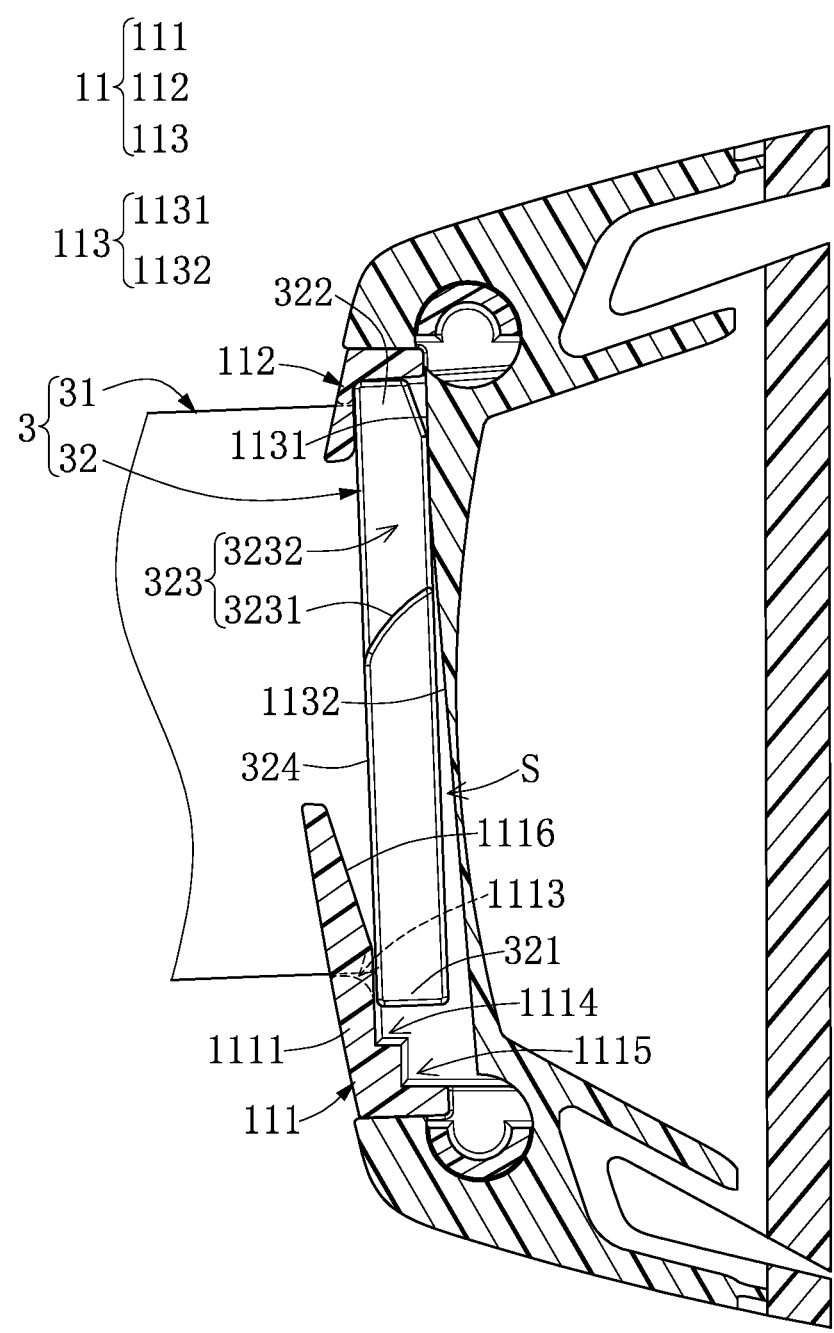
FIG. 9 is a cross-sectional view showing the buckling structure that is assembled with the inserting member.
Figure 10:
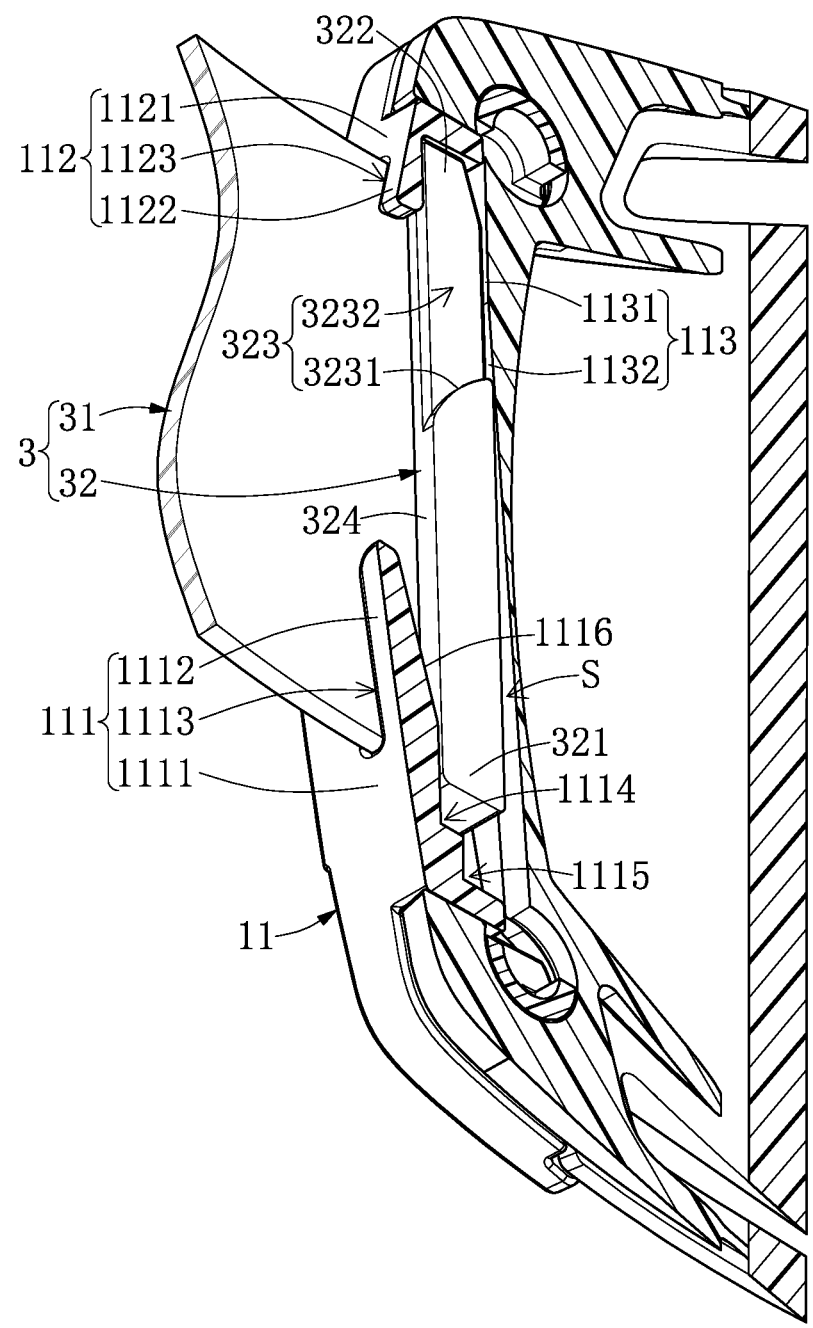
FIG. 10 is a perspective view of FIG. 9.
Figure 11:
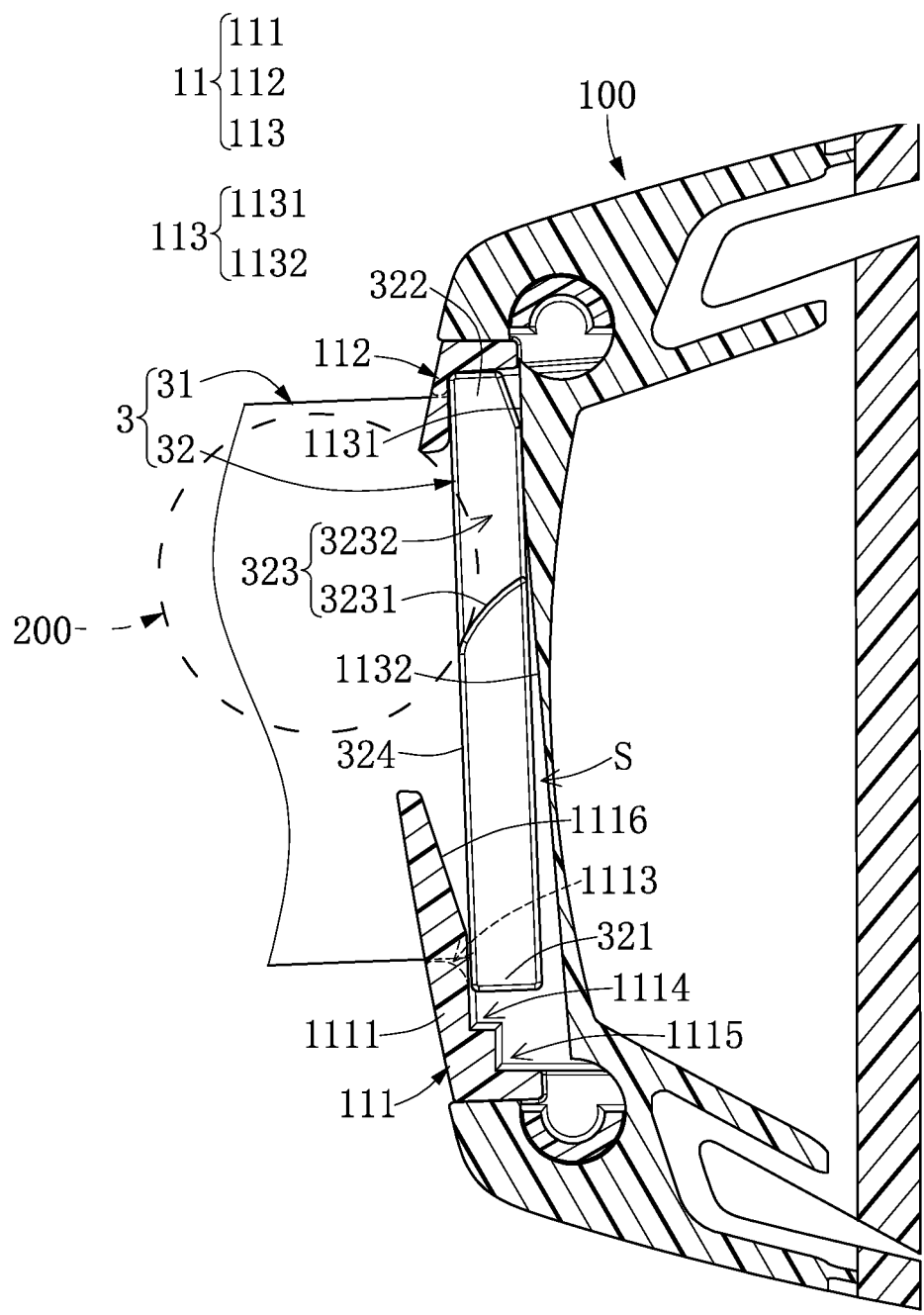
FIG. 11 is a cross-sectional view showing the buckling structure and the inserting member that can be disassembled from each other by a flat structure.
Figure 12:
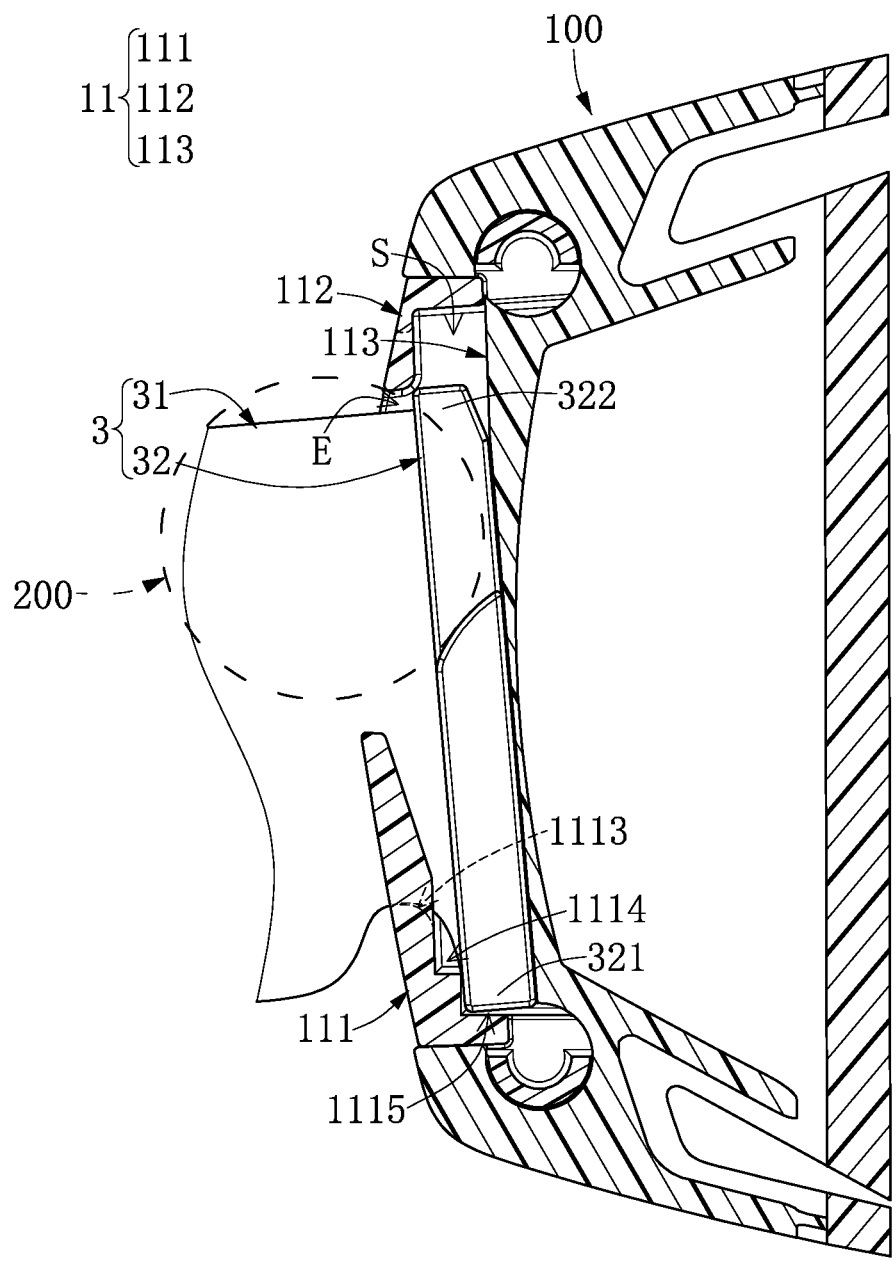
FIG. 12 is a cross-sectional view showing the buckling structure and the inserting member, the latter one of which is moved relative to the buckling structure by the flat structure.

As shown in FIG. 6 to FIG. 10, when the front end portion 321 of the inserting member 32 is inserted into the accommodating space S by passing through the entrance E, the front end portion 321 is guided by the guiding surface 1116 to move toward the inner surface of the front positioning portion 111 (e.g., the second step 1115), and a first portion of the belt body 31 adjacent to the front end portion 321 is resiliently squeezed by the bottom of the front slit 1113 of the front positioning portion 111, so that the squeezed first portion of the belt body 32 drives the rear end portion 322 to move toward the inner surface of the rear positioning portion 112. Accordingly, when the inserting member 32 is at the locked position (as shown in FIG. 9 and FIG. 10), a movement of the inserting member 32 in the accommodating space S of the buckling structure 11 is restricted by the front positioning portion 111 and the rear positioning portion 112.

As shown in FIG. 9 and FIG. 10, when the inserting member 32 is at the locked position, the relationship between the inserting member 32 and the buckling structure 11 is approximately disclosed as follows. A part of the top surface 324 arranged on the front end portion 321 abuts against the inner surface of the front positioning portion 111 (e.g., the first step 1114), and is arranged apart from the slanting segment 1132 of the bottom wall 113. The rear end portion 322 abuts against the inner surface of the rear positioning portion 112 (e.g., two opposite sides of the top surface 324 arranged on the rear end portion 322 respectively abut against the two rear retaining ribs 1122), and abuts against the plane segment 1131 of the bottom wall 113.

Moreover, the first portion of the belt body 31 is partially inserted into the front slit 1113, and a second portion of the belt body 31 adjacent to the rear end portion 322 of the inserting member 32 is partially inserted into the rear slit 1123. The first step 1114 of the front positioning portion 111 is arranged adjacent to the belt body 31, and the second step 1115 is arranged away from the belt body 31. When the first portion of the belt body 31 adjacent to the front end portion 321 is resiliently squeezed by the front positioning portion 111 (e.g., the bottom of the front slit 1113), the squeezed first portion of the belt body 31 generates an elastic force to drive the front end portion 321 to be disposed on the first step 1114, thereby effectively maintaining the relative position of the inserting member 32 and the buckling structure 11.

In addition, the concave portion 323 of the inserting member 32 is arranged adjacent to the unlocking rib 1122. When a flat structure 200 is inserted into a space (e.g., the notch 3232) surroundingly defined by the concave portion 323 and the unlocking rib 1122 and presses the arced surface 3231 of the concave portion 323 and the unlocking rib 1122, the inserting member 32 moves from the locked position to the unlocked position. The unlocking rib 1122 in the present embodiment is defined as an immovably fixed component.

Figure 13:
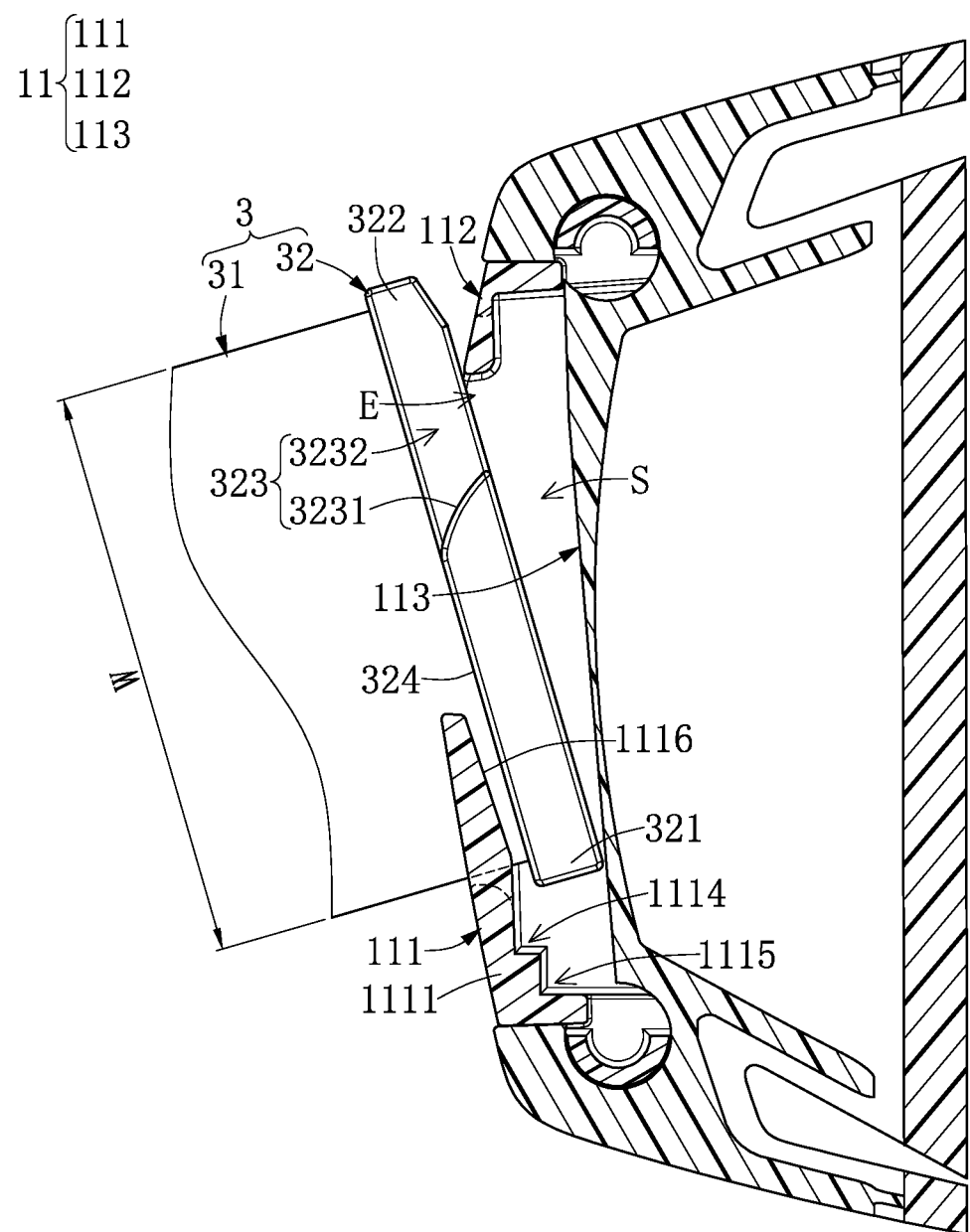
FIG. 13 is a cross-sectional view showing the buckling structure and the inserting member, the latter one of which is disassembled from the buckling structure by the flat structure.

Specifically, as shown in FIG. 9 to FIG. 13, when the inserting member 32 (e.g., the arced surface 3231 of the concave portion 323) at the locked position is pressed by the flat structure 200 (e.g., a coin), the front end portion 321 of the inserting member 32 separates from the front positioning portion 111 (e.g., the first step 1114) and moves along the slanting segment 1132 in a direction away from the rear positioning portion 112 (or moves toward the second step 1115), and the rear end portion 322 separates from the rear positioning portion 112 (e.g., the two rear retaining ribs 1122) and moves to an outer side of the accommodating space S by passing through the entrance E, so that the inserting member 322 can be located at the unlocked position (as shown in FIG. 13).

In other words, when the front end portion 321 of the inserting member 32 separates from the first step 1114 of the front positioning portion 111 and abuts against the second step 1115, the inserting member 32 receives an outwardly external force to separate the rear end portion 322 from the two rear retaining ribs 1122 of the rear positioning portion 112, so that the rear end portion 322 can move to an outer side of the accommodating space S by passing through the entrance E.

Figure 14:
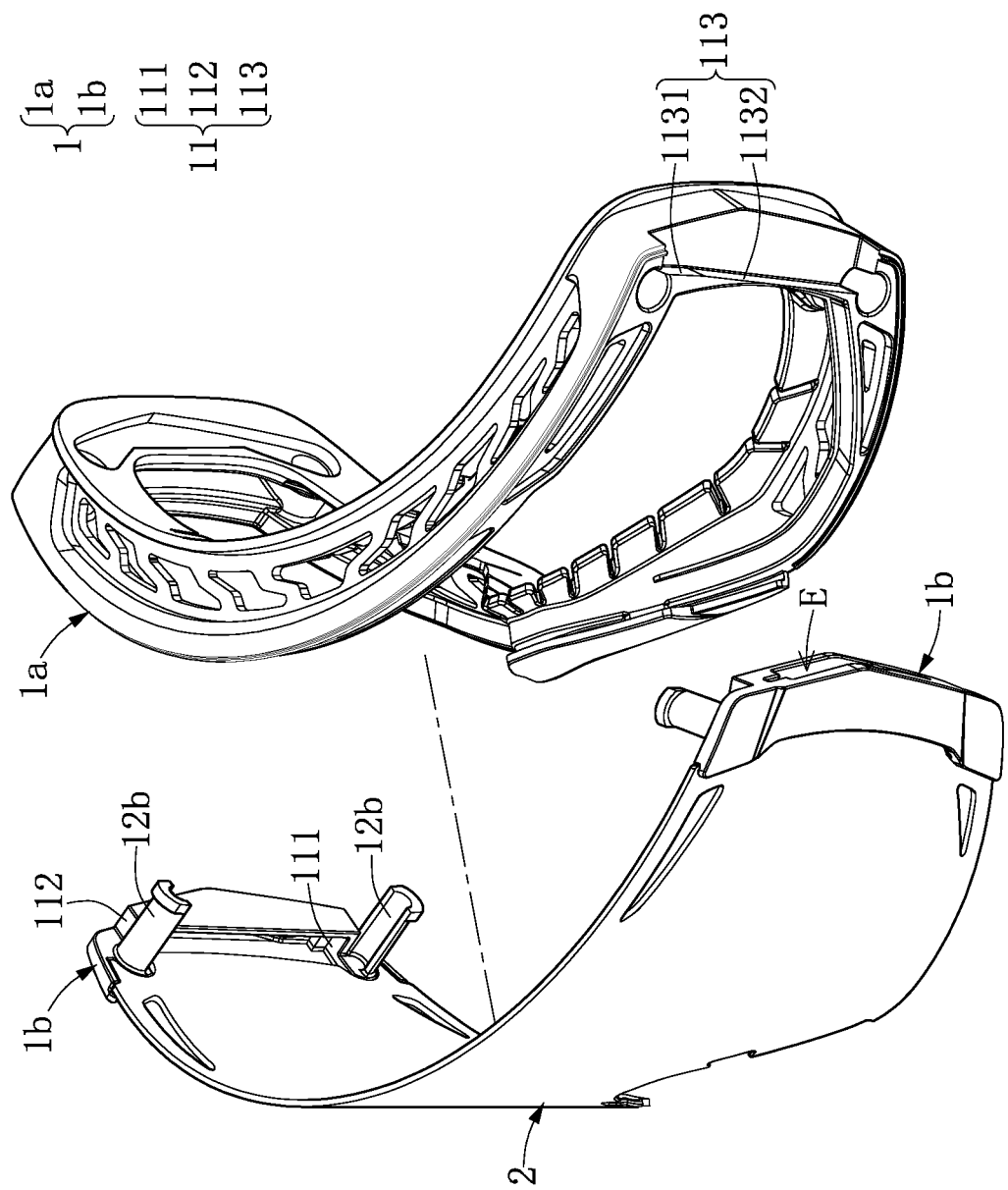
FIG. 14 is an exploded view of the goggle device with a detachable belt being omitted.
Figure 15:
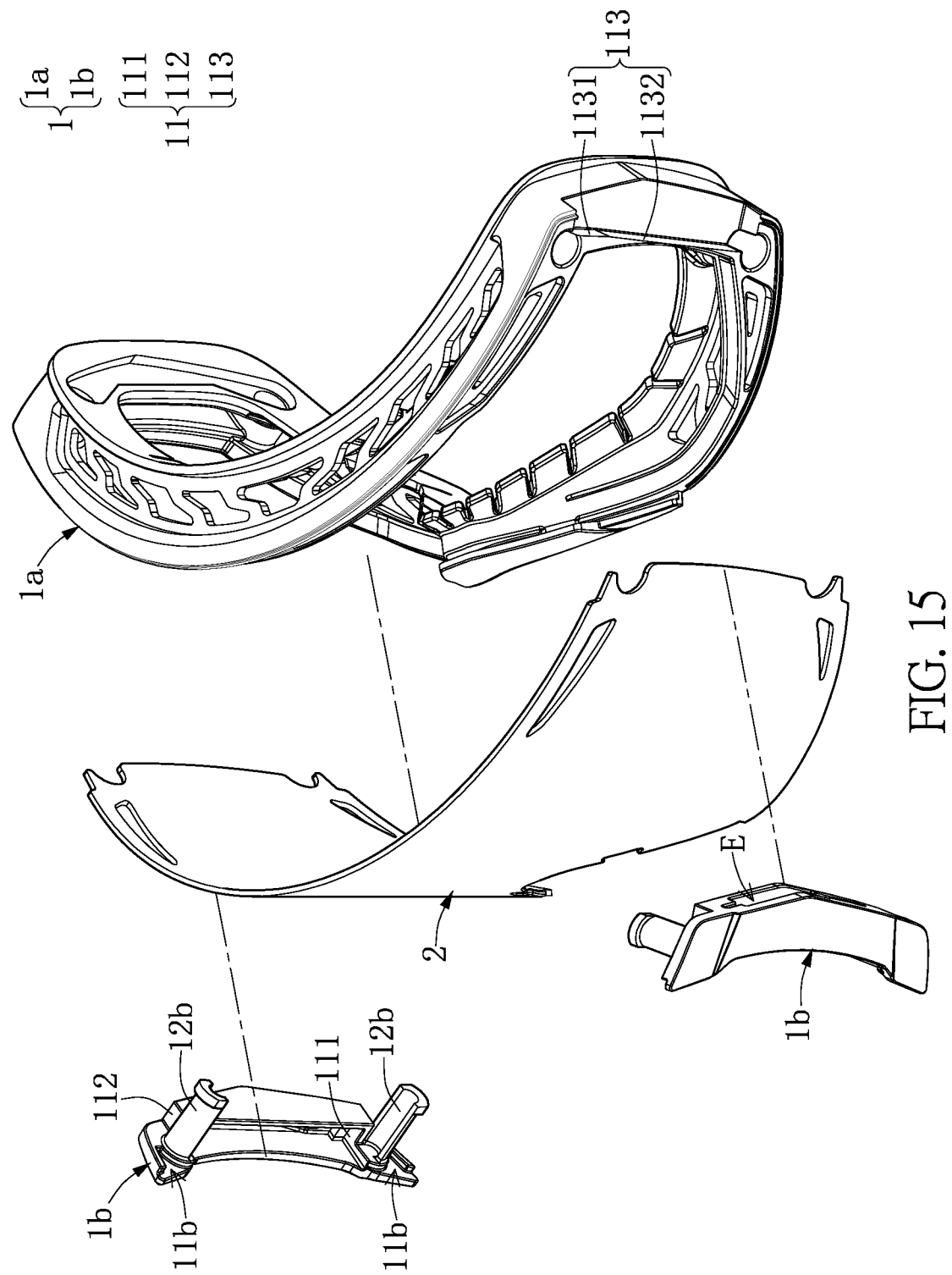
FIG. 15 is another exploded view of the goggle device with the detachable belt being omitted.

It should be noted that, the buckling structure 11 in the above description is regarded as a single component, but the buckling structure 11 in the present embodiment is formed by assembling three components. As shown in FIG. 14 and FIG. 15, the spectacle frame 1 in the present embodiment includes a main frame 1a and two positioning members 1b fastened to the main frame 1a. The two positioning members 1b are cooperated with the main frame 1a so as to respectively define the two buckling structures 11, and two opposite portions of the lens 2 are fastened to the main frame 1a through the two positioning members 1b, respectively, but the present disclosure is not limited thereto.

Specifically, a side portion of each of the two positioning members 1b (e.g., an outer portion of the positioning member 1b as shown in FIG. 15) is formed with a portion of the buckling structure 11 that excludes the bottom wall 113, and the other side portion of each of the two positioning members 1b (e.g., an inner portion of the positioning member 1b as shown in FIG. 15) has two edge grooves 11b and two engaging posts 12b corresponding in position to the edge grooves 11b.

Moreover, the two engaging posts 12b of each of the two positioning members 1b are detachably inserted into the main frame 1a, so that the two opposite portions of the lens 2 are respectively sandwiched between the two positioning members 1b and the main frame 1a. The two opposite portions of the lens 2 are respectively received in the edge grooves 11b of the two positioning members 1b, and are respectively engaged with the engaging posts 12b of the two positioning members 1b.

In addition, the buckling structure 11 in the present embodiment is formed by assembling three components, but the present disclosure is not limited thereto. For example, in other embodiments of the present disclosure, the buckling structure 11 can be a single component or can be formed by assembling two or more than three components.

In conclusion, the spectacle frame 1 of the goggle device 100 in the present disclosure is formed with the buckling structure 11 that is cooperated with an inserting member 32 and a belt body 31, so that the buckling structure 11 can be stably assembled with the detachable belt 3. Accordingly, the detachable belt 3 on the spectacle frame 1 of the goggle device 100 in the present disclosure can be changed according to different requirements, so that the goggle device 100 can have various appearances.

Moreover, the disassembling of the buckling structure 11 and the corresponding inserting member 32 is implemented by inserting a flat structure 200 into the buckling structure 11 as so to press the inserting member 32, thereby effectively preventing the inserting member 32 from separating from the buckling structure 11. In other words, each of the buckling structure 11 and the corresponding inserting member 32 are jointly formed as an unlock mechanism that is arranged in the accommodating space S (or the spectacle frame 1), thereby preventing the detachable belt 3 from separating from the spectacle frame 1 of the goggle device 100 by a non-unlock mechanism (e.g., collision).

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A goggle device, comprising:
a spectacle frame including two buckling structures respectively arranged on two opposite ends of the spectacle frame, wherein each of the two buckling structures has an accommodating space and an entrance that is in spatial communication with the accommodating space, and wherein each of the two buckling structures includes a front positioning portion and a rear positioning portion, wherein the front positioning portion is arranged at a first side of the entrance and the rear positioning portion is arranged at a second side of the entrance opposite the first side of the entrance, and wherein each of the two buckling structures includes a bottom wall facing the entrance;
a lens fastened to the spectacle frame; and
a detachable belt detachably assembled with the two buckling structures, and the detachable belt including:
an elongated and flexible belt body; and
two inserting members, wherein a first inserting member of the two inserting members is fixed on a first end of the belt body, and a second inserting member of the two inserting members is fixed on a second end of the belt body opposite the first end, wherein each of the two inserting members includes a front end portion and a rear end portion, and wherein the front end portion and the rear end portion are arranged respective on opposing portions of a respective one of the two inserting members, and the first inserting member is inserted into a first buckling structure of the two buckling structures, and the second inserting member is inserted into a second buckling structure of the two buckling structures so as to be at a locked position, wherein the first buckling structure and the second buckling structure of the two buckling structures and the first inserting member and the second inserting member of the two inserting members, when the front end portion is inserted into the accommodating space by passing through the entrance, the front end portion moves toward an inner surface of the front positioning portion, and a first portion of the belt body adjacent to the front end portion is squeezed by a front slit of the front positioning portion that is in spatial communication with the entrance and the accommodating space, so that the first portion of the belt body that is squeezed drives the rear end portion to move toward an inner surface of the rear positioning portion, and wherein when each of the two inserting members is at the locked position, a movement of the first and second inserting members in the accommodating space of the first and second buckling structures is restricted by the front positioning portion and the rear positioning portion.

2. The goggle device according to claim 1, wherein in the first buckling structure and the second buckling structure of the two buckling structures and the first inserting member and the second inserting member of the two inserting members, the inner surface of the front positioning portion includes a first step arranged adjacent to the belt body and a second step arranged away from the belt body, and when the first portion of the belt body adjacent to the front end portion is squeezed by the front positioning portion, the first portion of the belt body that is squeezed generates a force to drive the front end portion to be disposed on the first step.

3. The goggle device according to claim 2, wherein each of the two inserting members is configured to be pressed by a flat structure so as to move from the locked position to an unlocked position, and wherein when one of the two inserting members at the locked position is pressed by the flat structure, the front end portion separates from the first step and moves toward the second step, and the rear end portion separates from the rear positioning portion and moves to an outer side of the accommodating space by passing through the entrance, so that the respective one of the two inserting members is located at the unlocked position.

4. The goggle device according to claim 2, wherein in the first buckling structure and the second buckling structure of the two buckling structures and the first inserting member and the second inserting member of the two inserting members, the bottom wall includes a plane segment arranged adjacent to the rear positioning portion and a slanting segment extending from the plane segment, the rear end portion abuts against the plane segment, and the front end portion is arranged apart from the slanting segment.

5. The goggle device according to claim 4, wherein the plane segment and the slanting segment of each of the two buckling structures have an angle between the plane segment and the slanting segment.

6. The goggle device according to claim 4, wherein each of the two inserting members is configured to be pressed by a flat structure so as to move from the locked position to an unlocked position, and wherein when one of the two inserting members at the locked position is pressed by the flat structure, the front end portion separates from the first step and moves along the slanting segment in a direction away from the rear positioning portion, and the rear end portion separates from the rear positioning portion and moves to an outer side of the accommodating space by passing through the entrance, so that the respective one of the two inserting members is located at the unlocked position.

7. The goggle device according to claim 1, wherein in each of the two buckling structures, the rear positioning portion includes a rear base and two rear retaining ribs that extend from the rear base toward the entrance, the rear base and the two rear retaining ribs jointly define a rear slit that is in spatial communication with the entrance and the accommodating space, and one of the two rear retaining ribs is defined as a unlocking rib; and in the first buckling structure and the second buckling structure of the two buckling structures and the first inserting member and the second inserting member of the two inserting members, when a second portion of the belt body adjacent to the rear end portion is partially inserted into the rear slit, the two rear retaining ribs abut against two opposite sides of the rear end portion, each of the two inserting members has a concave portion recessed in the rear end portion and arranged adjacent to the unlocking rib, and when a flat structure is inserted into a space surroundingly defined by the concave portion and the unlocking rib and presses the concave portion and the unlocking rib, the respective one of the two inserting members moves from the locked position to the unlocked position.

8. The goggle device according to claim 7, wherein in the first buckling structure and the second buckling structure of the two buckling structures and the first inserting member and the second inserting member of the two inserting members, the inner surface of the front positioning portion includes a first step arranged adjacent to the belt body and a second step arranged away from the belt body, and when the first portion of the belt body adjacent to the front end portion is squeezed by the front positioning portion, the first portion of the belt body that is squeezed generates a force to drive the front end portion to be disposed on the first step; in the first buckling structure and the second buckling structure of the two buckling structures and the first inserting member and the second inserting member of the two inserting members, the bottom wall includes a plane segment arranged adjacent to the rear positioning portion and a slanting segment extending from the plane segment, the rear end portion abuts against the plane segment, and the front end portion is arranged apart from the slanting segment; and when the concave portion of one of the two inserting members at the locked position is pressed by the flat structure, the front end portion separates from the first step and moves toward the second step along the slanting segment, and the rear end portion separates from the two rear retaining ribs and moves to an outer side of the accommodating space by passing through the entrance, so that the respective one of the two inserting members is located at the unlocked position.

9. The goggle device according to claim 1, wherein the spectacle frame includes a main part and two positioning members fastened to the main part, the first buckling structure is formed on a first ore of the two positioning members and a first corresponding portion of the main part, and the second buckling structure is formed on a second one of the two positioning members and a second corresponding portion of the main part, and two opposite portions of the lens are fixed at the main frame part through the two positioning members, respectively.

10. A buckling module of a goggle device, comprising:
a buckling structure having an accommodating space and an entrance that is in spatial communication with the accommodating space, wherein the buckling structure includes a front positioning portion and a rear positioning portion, wherein the front positioning portion is arranged at a first side of the entrance and the rear positioning portion is arranged at a second side of the entrance opposite the first side of the entrance, and wherein the buckling structure includes a bottom wall facing the entrance; and
a flexible belt body and an inserting member that is fixed on an end of the belt body, wherein the inserting member includes a front end portion and a rear end portion, and wherein the front end portion and the rear end portion are arranged respective on opposing portions of the inserting member, and the inserting member is inserted into the buckling structure so as to be at a locked position, wherein when the front end portion of the inserting member is inserted into the accommodating space by passing through the entrance, the front end portion moves toward an inner surface of the front positioning portion, and a first portion of the belt body adjacent to the front end portion is squeezed by a front slit of the front positioning portion that is in spatial communication with the entrance and the accommodating space, so that the first portion of the belt body that is squeezed drives the rear end portion to move toward an inner surface of the rear positioning portion, and wherein when the inserting member is at the locked position, a movement of the inserting member in the accommodating space of the buckling structure is restricted by the front positioning portion and the rear positioning portion.

\* \* \* \* \*